United States Patent [19]
Coleman et al.

[11] Patent Number: 5,560,830
[45] Date of Patent: Oct. 1, 1996

[54] SEPARATOR FLOAT AND TUBULAR BODY FOR BLOOD COLLECTION AND SEPARATION AND METHOD OF USE THEREOF

[76] Inventors: Charles M. Coleman, 958 Washington Rd., Pittsburgh, Pa. 15228; William Kendrick, 34 Willowbrook Dr., Doylestown, Pa. 18901

[21] Appl. No.: 354,649

[22] Filed: Dec. 13, 1994

[51] Int. Cl.$^6$ .......................... B01D 17/038; B01D 17/02
[52] U.S. Cl. .......................... 210/695; 210/121; 210/514; 210/516; 210/789; 422/72; 422/101; 436/45; 494/16
[58] Field of Search .................................. 210/121, 223, 210/512.1, 516, 695, 782, 787, 789; 422/72, 73, 101, 102; 436/45, 177; 494/16, 36, 37; 277/23, 34, 80, 228; 49/477.1, 478.1; 137/409; 446/153

[56] References Cited

U.S. PATENT DOCUMENTS

| | | |
|---|---|---|
| 2,760,302 | 8/1956 | Cheskin ................................ 446/153 |
| 2,952,462 | 9/1960 | Planin ................................... 446/153 |
| 3,508,653 | 4/1970 | Coleman . |
| 3,647,070 | 3/1972 | Adler . |
| 3,779,383 | 12/1973 | Ayres . |
| 3,786,985 | 1/1974 | Slaivas . |
| 3,814,248 | 6/1974 | Lawhead . |
| 3,852,194 | 12/1974 | Zine, Jr. . |
| 3,931,018 | 1/1976 | North, Jr. ............................. 210/359 |
| 4,027,660 | 6/1977 | Wardlaw et al. . |
| 4,055,501 | 10/1977 | Cornell ................................ 210/316 |
| 4,077,396 | 3/1978 | Wardlaw et al. . |
| 4,101,422 | 7/1978 | Lamont et al. . |
| 4,137,755 | 2/1979 | Wardlaw et al. . |
| 4,140,631 | 2/1979 | Okuda et al. . |
| 4,148,764 | 3/1979 | Lamont et al. ....................... 260/22 |
| 4,152,270 | 5/1979 | Cornell ................................. 210/516 |
| 4,159,896 | 7/1979 | Levine et al. . |
| 4,172,803 | 10/1979 | Ichikawa et al. ..................... 252/60 |
| 4,180,465 | 12/1979 | Murty ................................... 210/516 |
| 4,190,535 | 2/1980 | Luderer et al. . |
| 4,816,168 | 3/1989 | Carrol .................................. 210/782 |
| 4,818,418 | 4/1989 | Saunders ............................. 210/782 |
| 4,844,818 | 7/1989 | Smith ................................... 210/789 |
| 4,867,887 | 9/1989 | Smith ................................... 210/782 |
| 4,877,520 | 10/1989 | Burns ................................... 210/94 |
| 4,946,601 | 7/1990 | Fiehler ................................. 210/782 |
| 4,957,638 | 9/1990 | Smith ................................... 210/782 |
| 5,030,341 | 7/1991 | McEwen ............................... 210/94 |

(List continued on next page.)

OTHER PUBLICATIONS

"A rapid tecnique for the preparation of cell–free blood serum plasma" by H. Harold Nishi, Clin. Chim. Acta. 11, (1965), Table of Contents, pp. 290,292.

"New Hydrophilic Polyester–Ester–Amide Block Copolymers" by D. G. Davis and J. B. Conkey, Presented at the Annual Technical Meeting of SPE, 1992, pp. 622–627 and attachments.

Atochem Brochure entitled PEBAX Polyether block amide . . . a unique family of engineering thermoplastic elastimers, undated.

Primary Examiner—Joseph W. Drodge
Attorney, Agent, or Firm—Buchanan Ingersoll, P.C.; Lynn J. Alstadt

[57] ABSTRACT

A separator float has a generally cylindrical body and a water swellable band having a selected outer diameter fitted circumferentially around a portion of the generally cylindrical body. The water swellable band is made of a water swellable material so that upon being exposed to water the water swellable band swells to a greater outside diameter. The separator float is preferably used in a blood collection tube and has a specific gravity between specific gravities of a light phase and a heavy phase of the blood. After the blood has been collected and centrifuged the separator float moves to a position between the light phase and the heavy phase and the water swellable band is exposed to water in the blood causing the band to swell and create a seal. Thereafter, the serum or plasma as well as white blood cells, lymphocytes, monocytes and platelets can be removed from the blood collection tube.

17 Claims, 4 Drawing Sheets

U.S. PATENT DOCUMENTS

| | | | |
|---|---|---|---|
| 5,053,134 | 10/1991 | Luderer et al. | 210/516 |
| 5,065,768 | 11/1991 | Coleman et al. | 128/760 |
| 5,236,604 | 8/1993 | Fiehler | 210/782 |
| 5,242,803 | 9/1993 | Burtis et al. | 436/45 |
| 5,269,927 | 12/1993 | Fiehler | 210/516 |
| 5,322,659 | 1/1994 | Walder et al. | 264/171 |

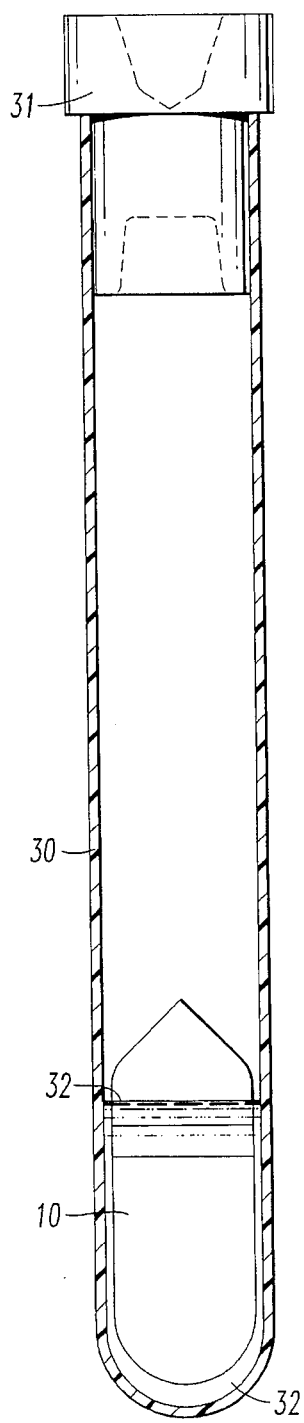
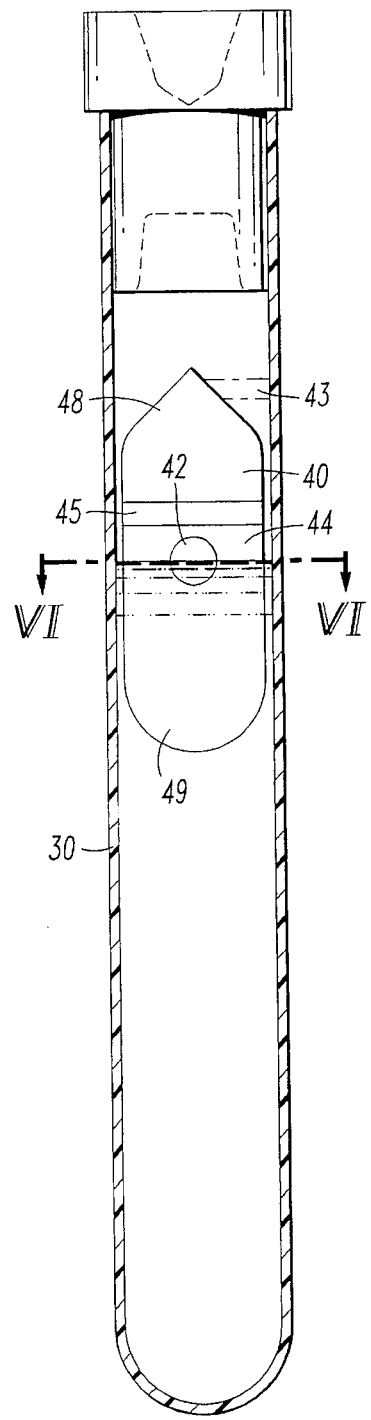
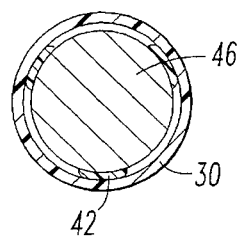
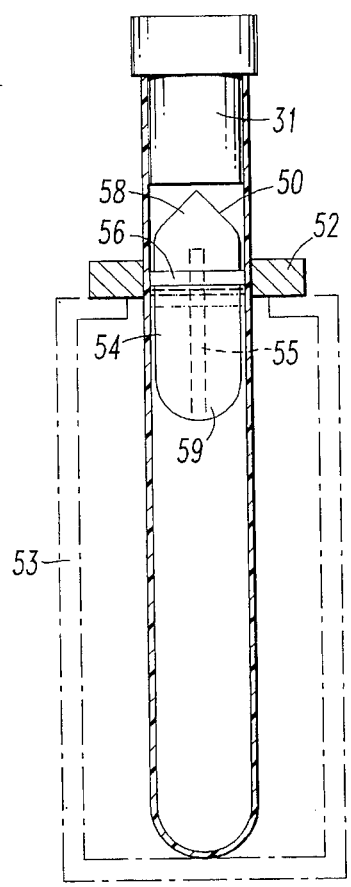

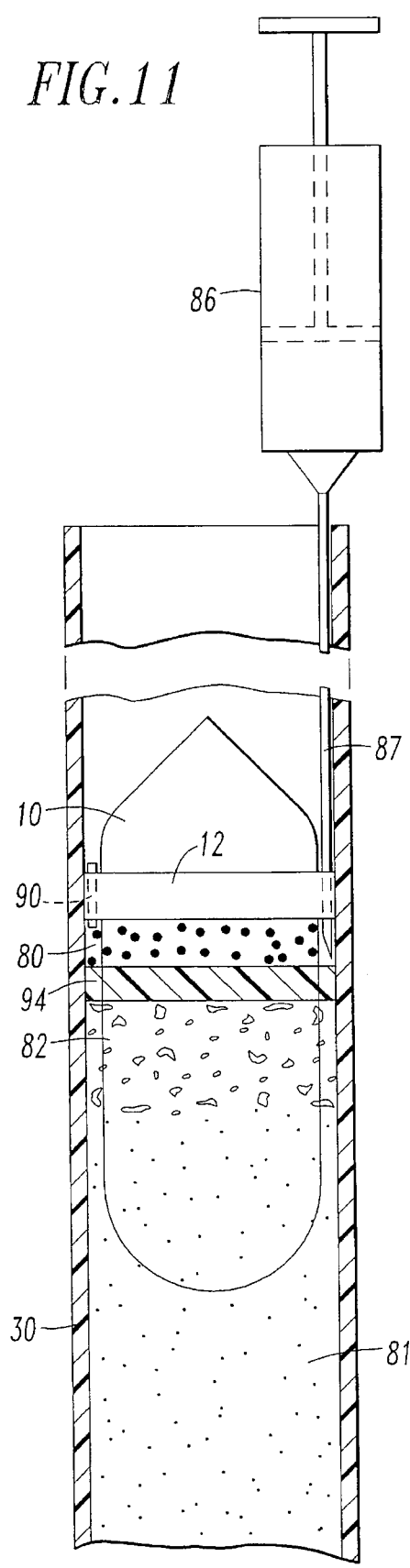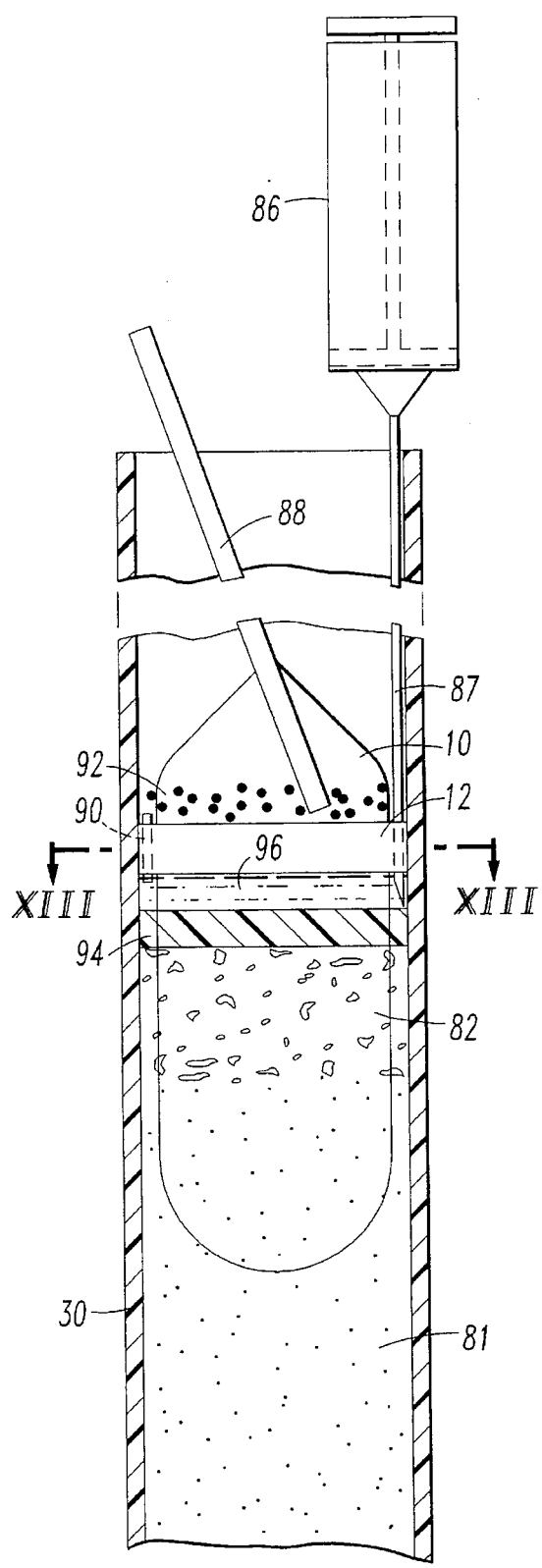

5,560,830

SEPARATOR FLOAT AND TUBULAR BODY FOR BLOOD COLLECTION AND SEPARATION AND METHOD OF USE THEREOF

BACKGROUND OF THE INVENTION

1. Field of the Invention

The invention is related to methods and apparatus to separate, and isolate for testing, serum or plasma, red cells, and white cells in evacuated blood collection tubes; obtaining oil free plasma or serum; and harvesting of white cells.

2. Brief Description of the Prior Art

Human blood is routinely collected in sealed, evacuated test tubes and centrifuged to separate the lighter serum or plasma portion from the heavier red blood cells. Typically a portion of the serum or plasma is then removed and tested. While the separated blood is stored awaiting testing certain chemicals can migrate between the separated layers giving incorrect test results. Consequently, the art has developed a variety of separators having a specific gravity between the serum or plasma and the red blood cells. These separators are either solid devices or gels.

The first solid separator was disclosed in U.S. Pat. No. 3,508,653 to Coleman. That device was a rubber or other elastomeric cylinder. A major problem with that device was the inability to maintain a seal because it is costly to maintain the precise inner diameter of the test tube when mass produced. The separator of Lawhead's U.S. Pat. No. 3,814,248 was the next solid separator development following Coleman's invention. Lawhead's separator is a centrifugally motivated spool originating from and placed adjacent to a vacuum maintaining stopper. There is also a polystyrene sphere free and unconstricted within the hollow inside of the tube. In use, blood is collected in the tube and is centrifuged. That action induces the free sphere to move under centrifugal force to join the socket-like underside of the floating rubber spool at the interface of the heavy and light phases. This product was unable to be used for the harvesting of serum because the floating ball frequently became enmeshed in the clot, preventing enclosure of the valve-like separator. Further, the separator did not seal firmly enough to withstand more than mild shock to the tube of separated blood, resulting in remixing of plasma and cells during transport, and other handling.

Ayres' U.S. Pat. No. 3,779,383 describes a complicated, costly device in which the blood introduction end of the tube is opposite to the movable separator end of the tube, and abutting an impenetrable rubber closure. Ayres' embodiment was unable to provide interface separation of the light and heavy phases of the blood because the separation element did not possess a specific gravity intermediate the two phases, but relied on an arbitrary stop element molded into the collection tube, combined with a centrifugally operated element having a specific gravity considerably higher than the blood cells. Blaivas was issued U.S. Pat. No. 3,786,985 for a device very similar to the Ayres' collection tube, excepting that the centrifugally motivated separator element abutted the needle penetrable stopper.

North in U.S. Pat. No. 3,931,018 discloses a solid separator for use in separation of blood serum and blood plasma using centrifugal force that must be inserted into the blood collection tube after blood collection. This device has a disc filter element above the solid separator having a specific gravity intermediate the light and heavy phases. The product has not attained significant acceptance because it is less convenient and less efficient to use and compromises sterility. Others have made centrifugally motivated solid separator devices of various configurations including a hollow, piston-like, coaxial tube disclosed in U.S. Pat. No. 4,159,896 to Levine et al., or ring disclosed in U.S. Pat. No. 5,236,604 to Fiehler, a closed end coaxial tube disclosed in U.S. Pat. No. 4,946,601 to Fiehler, an umbrella shaped solid separator device designated to ascend to the interface during centrifugation disclosed in U.S. Pat. No. 4,152,270 to Cornell, and a dual component assembly having a rigid conical core surrounded by a cup-shaped elastomeric component disclosed in U.S. Pat. No. 4,877,520 to Burns. Tubes containing these separators are limited in their function, and cannot be used for transport, or with many of the newer large high through-put analyzers.

J. A. McEwen, et al, in U.S. Pat. No. 5,030,341, disclose a solid separator system in which blood collection tubes are rotated on their axis to centrifuge the contents, rather than in the conventional way in which a blood filled tube is rotated with the tube's axis and contents rotate perpendicular to the centrifuge's axis of rotation. Such a system does not appear to be economical, since a complete change in equipment requirements, particularly the centrifuge device must be made. The system also requires relatively expensive disposable collection tubes.

As a result of the difficulty in designing what has been considered a commercially viable solid separator, manufacturers have resorted to the use of semi-solid, or thixotropic gel materials. A thixotropic gel is used in this context to mean a material formulated to remain rigid enough to remain in place, i.e., "firm", or "solid", until an external stress, such as a centrifugal force is applied. In a vacuum collection tube containing blood and gel, centrifugation of the tube at the proper level of acceleration (g force) would cause the gel to deform, flow to the interface between the packing cells and the lighter liquid phase, and finally come to a stable settled state reformed into a disc or cylindrical segmented barrier between the heavy phase, and the light phase.

Lukacs and Jacoby (U.S. Pat. Nos. 3,780,935 and 3,963,119) introduced the use of a very viscous silicone separator material prepared by intimate mixing of silicone oil and amorphous silica in proper proportions to yield a highly viscous sealant material having a specific gravity in the range between the specific gravity of the light phase and the specific gravity of the heavy phase of blood. They claim the silicone material in these patents, used with a funnel-like device inserted into the tube of collected blood, flows into the centrifugally separating blood, forming a barrier layer of viscous silicone oil and silica material with a specific gravity about 1.03 to 1.05. This product, sold under the trademark "SURE-SEP", provides a poor seal because the composition is not a firm gel and flows under gravitational force alone. It has the great disadvantage of needing to be inserted after the blood has been collected and not being an element assembled and integrated into the blood collection tube.

A further approach is the addition of granulated or powdered materials having a specific gravity intermediate the light and heavy blood phases to tubes of collected whole blood, followed by centrifugation, for separation of the heavy and light phases of the blood. Use of insoluble small particles of the desired specific gravity first described by Nishi in 1965, *Clin. Chem. Acta*, 11 (1965) pp. 290–292. Another modification of this technique was patented by Adler in U.S. Pat. No. 3,647,070. Adler added water-swellable, non-ionic hydrophilic polyhydroxyethylmethacrylates or polyacrylamide hydrogels in granulated or disc form, with a specific gravity between the two centrifuged, separated phases. These materials were added to blood collection tubes only after centrifugation to provide for a barrier between the heavy and light phases. Neither case provides for an integrated blood collection tube that permits a separation of whole blood collected, without the transference of plasma through the interstices. The blood corpuscles squeeze through the gaps between the solid particles, even when swollen and compacted after centrifugation. Further, the granulated separator mass is readily broken by impact, or unusual movement, and the container must be protected from shock during transport.

Zine, received U.S. Pat. No. 3,852,194 for the apparatus and method of using a silicone oil containing a silica thixotropic composition in a vacuum blood collection tube. The tube assembly with the silica/silicone oil gel composition in a vacuum collection tube uses an energizer plunger to move the gel toward it's sealing position between the separated phases. Subsequent to that patent there has been much development of an incremental nature intended to formulate many subspecies of silicone gels having desirable properties such as radiation stability. These efforts have generally been directed to mixing silicone oil with amorphous silica, and often a surfactant for gel network formation and maintenance. Usually, hydrophobic amorphous silica particles were used to provide optimal conditions of stability of the thixotropic material, along with the desired specific gravity, and stabile viscosity. Other manufacturers later replaced the original dimethylsiloxane (silicone) oils with other organic oils to compound thixotropic gels from amorphous silica.

Difficulties in providing silicone gel commercial products, have caused abandonment of this material for use in blood separator assemblies by Sherwood, Becton Dickinson, and the original group that introduced the Lukacs and Jacoby products, General Diagnostics. U.S. Pat. Nos. 4,021,340 and 4,180,465 have been issued for thixotropic blood separator gels using polybutene in lieu of dimethylsiloxane oil for use in mixing with amorphous silica. Becton Dickinson replaced silicone oil based gels around 1980 using gels based on polyester oil in the "SST" product following the teaching of Lamont and Braun in U.S. Pat. Nos. 4,101,422 and 4,148,764. This polyester gel, and virtually all commercial thixotropic gels, require mixing an oil with amorphous, usually hydrophobic silica to adjust specific gravity and to ensure thixotropy. Following the same trend of mixing a base oil with silica, the Terumo Corporation obtained U.S. Pat. No. 4,172,803 for a gel containing four additional butene related polymers.

Okuda, Abo, and Shinohara were issued U.S. Pat. No. 4,140,631 for a sealant comprising alkyl acrylates or methacrylates as sealants, claiming a significant advantage of clarity, and ability to dispense with the need for amorphous silica. In this case a high viscosity Newtonian sealant is the result. If amorphous silica is added the resultant sealant becomes a thixotropic gel which will be practically transparent.

Mendershausen has demonstrated the existence of serious problems associated with the use of gel compositions of oil and silica when used as separators in blood collection tubes. In the case of certain Eastman Kodak Products, oil globules have been seen in the light phase of the blood and oil films at the top of the light phase often seriously affect results of blood glucose ("blood sugar") tests. The oil can form a film on the test slides, causing blocked diffusion of the substance being analyzed into the slide.

In one Boehringer-Mannheim product, the BMC/Hitachi 747 Chemistry Analyzer, it was found that ion specific electrodes can cause reporting of spurious sodium levels in patients, because polyester oil droplets originating from gels float freely in the light phase of separated blood, or form oil films over the light phase of the blood. The oil is thereupon transferred onto electrode probes that are immersed into the light phases of the blood for testing. Mendershausen believes that the oil coating on the surface of the sodium electrode probe insulates the electrode, changing the electrical potential, and consequently the reported values of the sodium. Such changes on the sodium electrode can affect other electrodes (potassium, calcium, chloride, etc.) and can lead to grave problems resulting from the inaccuracies reported.

Separation of oil from the gel in blood separator tubes of oil has been noted by engineers in Sherwood assigned patents, earlier by Murty, and subsequently by Fiehler (U.S. Pat. Nos. 4,180,465, 4,946,601, 5,236,604, and 5,269,927) Solutions offered ranged from use of polybutene oil in place of silicone oil, isolation of the gel prior to blood collection, and the use of plastic oil capturing devices. In all the disclosures, the importance of the problem was restated and reoutlined, but no satisfactory solutions were provided because the root cause was not eliminated. Inevitably, blood separation tubes containing gel released oil during centrifugation, because all the gels comprise an inherently unstable mixture of two phases of materials, one is heavier than the heaviest phase of the blood, while the other (the oil) is lighter than the lightest phase of the blood and rises to the top.

Burns in U.S. Pat. No. 4,877,520 provides additional support for the need to replace gel separators with solid separators. At Column 1, lines 60–66, he states, "Moreover, the shelf-life of the product is limited in that globules are sometimes released from the gel mass or network. These globules have a specific gravity that is less than the separated serum and will float in the serum and can clog the measuring instruments, subsequently, during the clinical examination of the sample collected in the tube."

The use of silicone separator gel in evacuated blood collection tubes preceded a number of patents dealing with separation of lymphocytes and monocytes blood containing anticoagulants for testing purposes. A. A. Luderer et al, in U.S. Pat. Nos. 5,053,134 and 4,190,535, and W. C. Smith et al, in U.S. Pat. Nos. 4,957,638, 4,954,264, 4,867,887, and 4,844,818 all basically use gel separators of defined specific gravity to separate and isolate the mononuclear white cellular elements from the red cells of the blood. Many add other components to the gel base. These methods are feasible, but they are not necessarily simple, rapid, or particularly well suited to automation.

Wardlaw, et al, in U.S. Pat. Nos. 4,027,660 and 4,077,396 et seq., describe a blood testing device which expands the axial presentation of white blood cells in a small bore tube of blood upon centrifugation. This was used to provide a simple, rapid means to determine both total, and differential white blood counts. Such an invention has become the basis of widely used blood counting systems, often in a physician's office laboratory. Such a device is designed for diagnostic purposes only, since no means are provided to collect the various white blood cells separated in the system. Further, the devices contain stain to differentiate the type of white cells present in the tubes.

In our U.S. Pat. No 5,065,768 we disclose tubes with self-sealing plugs having an air vent channel which automatically seals a few seconds after the blood sample contacts the plug. The blood sample may then be dispensed with aid of a special pipette, or centrifuged in a microhematocrit or functionally similar centrifuge at about 11,000 g after collection of the fluid. This provides a packed cell volume reading, which may be followed by plasma dispensation from that tube. This invention is directed primarily toward the collection of blood from fingersticks, and discloses self-sealing plugs that seal off the air vent as a direct result of contact with the specimen at the time the sample is filled with blood from skin punctures. This invention does not relate to sealing devices that are intended to begin to seal during and after centrifugation has begun. Furthermore, the patent teaches that solid separators or gels are used to separate the phases of centrifuged blood.

Walder et al. in U.S. Pat. No. 5,322,659 disclose a two-layer tubing having a hydrophilic polymer outer layer. The tubing is dipped into a solution that carries anti-infective reagents or other agents which are absorbed by the polymer layer. There is no concern with a change in dimension after absorption of the solution. The tubing is then inserted into the body and there releases the reagent. These tubes are not intended or suitable for use as sealing devices.

There is a need for a simple, effective, and economical solid device for separation of serum and plasma. There is also a need for a solid separator to facilitate the harvesting of lymphocytes and monocytes in contemporary clinical laboratory testing for a multitude of immunological, genetic, microbiological, and other testing purposes as well as to aid collection of platelets and small white cells used in coagulation studies.

SUMMARY OF THE INVENTION

The present invention provides a solid separator which seals the separated blood phases in a blood collection tube. It requires minimal retraining for its use by phlebotomists and other healthcare workers collecting and separating blood. Being a solid separator device, and not a thixotropic gel mixture requiring both a light phase and a heavy phase as essential components, it will not release oil into the serum or plasma. Our device will not lead to obstruction or clogging of sample aspirator tubes. It will not lead to interference on dry chemistry slides from the oil released from thixotropic gels.

The method of the present invention provides for a centrifugally motivated separation of the light and heavy phases of blood previously collected within a tubular container and placement of a freely movable separator float of defined specific gravity between the two phases; followed by expansion of a peripheral sealing element of the float radially toward and against the inner wall of the tubular container over a time period to provide a stable, impact-resistant, non-contaminating, isolation of the separated phases within the tubular container.

The light phase can then be decanted or drawn from the tube. To collect monocytes, lymphocytes, platelets or small white cells a needle is inserted through the seal to draw these cells from below the sealing band. Alternatively, a second passageway could be provided through the sealing band so that a fluid injected through the needle would push the cells through the second passageway to a position above the seal. From there they could be drawn or decanted.

Our device utilizes a separator float that has a specific gravity between the light and heavy phases of the blood, preferably between 1.03 to 1.06. The separator float has a peripheral water swellable band generally flush and recessed within a molded float body. The specific gravity of the separator float is determined primarily by the specific gravity of the float body, and to a lesser amount by the water swellable band. The float body may be a single element, or a combination of subelements that taken together provide the desired specific gravity and other desired properties. For example, a magnetic separator float can be constructed from a combination of a molded polypropylene component and iron or steel elements to provide a separator float with combined specific gravity between 1.03 and 1.06.

The water swellable band of this invention may be fabricated from the category of materials described in our U.S. Pat. No. 5,065,768 as super absorbent materials dispersed within an organic or silicone elastomer support matrix. Cross-linked hydrogels fabricated from hydrophilic acrylic and acrylamide monomeric components and certain polyether-amide or certain polyether urethane block copolymers are also suitable. Thermoplastic polyurethane elastomers containing superabsorbents may also be used, but they tend to be more expensive and ion-exchanging. The block copolymers of ethylene oxide with polymides or polyurethanes are preferred because they can absorb water in amount from half to three times their weight, yet are non-ionic and thus will not affect the electrolyte values.

The assembly of the invention permits initial positioning of the separator float having a swellable band in the evacuated blood collection tube. Yet, the separator float does not become enmeshed in the coagulum during centrifugation, preventing its movement and emplacement between the two separated phases. In addition, the assembly of the invention provides for inhibition of premature actuation of the water swellable band, a frequent requirement for isolation of both plasma and serum light phases.

We prefer to provide two categories of separator isolation assemblies. The first is that in which plasma only is obtained, while the second is that in which both serum and plasma are obtained. In the case of plasma, the separator float may be located in the bottom of the tube, immersed in a bath of a relatively high specific gravity liquid so that the water swellable band is covered sufficiently to prevent blood collected by phlebotomy from coming into contact with it. The amount and specific gravity of the isolation liquid should permit both adequate immersion of the separator float, and sufficient coverage of the water swellable seal. If the specific gravity of the liquid is too high, buoyancy of the float will cause the band to be positioned above the liquid levels and the seal will not be sufficiently covered. Satisfactory liquids for this purpose are polymethyl-3,3,3-trifluorpropylene siloxane with a specific gravity range of 1.26 to 1.30 and viscosities from 1000 to 10,000 centipoises and polyadipate esters with specific gravities between 1.10 to 1.16 and viscosities between 2,000 and 30,000 centipoises.

If wicking of the blood is found to provide excessive premature swelling of the available seal, the separator float and the upper zone of the blood collection tube may both be coated with a viscous hydrophobic oil, with a specific gravity sufficiently greater than the specific gravity of the blood cells to drain off the separator float and sink below the blood cells at the time of centrifugation and so removed from interfering with the function of the tube and contamination of testing materials. Another method to isolate the water swellable band from contact with the blood, with its water causing premature swelling, is to jacket the band with a sleeve located in the upper end of the collection tube. Channels can be molded, or profiled in the sleeve if the part be extruded, so that blood might flow in the channels and fill the main body of the tube.

The preferred means to prevent wicking is to utilize localized elevations on the plastic or glass collection tube to isolate the body of the separator float from the wall by about 0.5 to 1.0 mm using ridges, conical points, or topological equivalents, in combination with a single attachment point, above the water swellable seal. Isolation of the float body from the inner tube wall can be made by several means, including deposition of a patch by hot melt adhesives, room temperature vulcanization materials, such as silicone cement, or by attachment of small pressure sensitive patches. However, it is preferred to incorporate the projections as integral components of the collection tube itself during tube manufacture either as part of the original molding process or during secondary localized thermoforming after the test tube is molded. The water swellable seal may also be coated with a hydrophobic oil, as noted above, which will serve to shed blood as it flows past the band into the tube cavity under vacuum. Attachment of the float to the tube wall at its forward end can be made by hot melt attachment, or any other suitable means known to those skilled in the art of fastening.

In the case where collection of whole blood is required, i.e., where serum is used for testing, the separator float must be positioned so that it will not become enmeshed in the clot after the blood has coagulated. In addition, the swellable band must not have sufficient blood contact to expand the band prematurely which would prevent correct emplacement of the separator float. Generally, most clinical laboratory centrifuges at this time cannot produce adequate g force to force the separator float through the clot, and become positioned between the serum and the clot to result in a clean insolation. Nevertheless, higher g force centrifuges are capable of thrusting the float through the clot and isolating the phases.

Our simplest assembly positions the separator float with its upper extremity far enough from the upper edge of the evacuated collection tube to avoid contact with the tip of the blood collecting cannula, which is about 10 to 15 mm from the bottom of a standard plug vacuum closure. The separator float may be suspended by pressure from ridges arising from the tube wall, elastomer hot melt, or silicone rubber tips or balls located on the inside wall of the tube against the float at the upper end of the evacuated tube. The blood can then clot without sufficient contact with the swellable band to cause malfunctions from excessive swelling.

Tubes may be made with closures at both ends, permitting direct sampling of the contents of both of the isolated compartments.

Other objects and advantages of the invention will become apparent from a description of the present preferred embodiments shown in the drawings.

BRIEF DESCRIPTION OF THE FIGURES

FIG. 4 is an elevational view of the separator float of FIG. 1 in a blood collection tube.

FIG. 5 is an elevational view of a second present preferred separator float in a blood collection tube.

FIG. 6 is a cross-sectional view taken along line VI—VI of FIG. 5.

FIG. 7 is an elevational view of a third present preferred separator float in a blood collection tube.

FIG. 11 is an elevational view of the separator float shown in FIG. 1 in a blood collection tube after the tube has been centrifuged, the plasma or serum has been removed and a needle has been inserted into a selected layer of cells.

FIG. 12 is a view similar to FIG. 11 after fluid has been injected through the needle.

DESCRIPTION OF THE PREFERRED EMBODIMENTS

Figure 1:
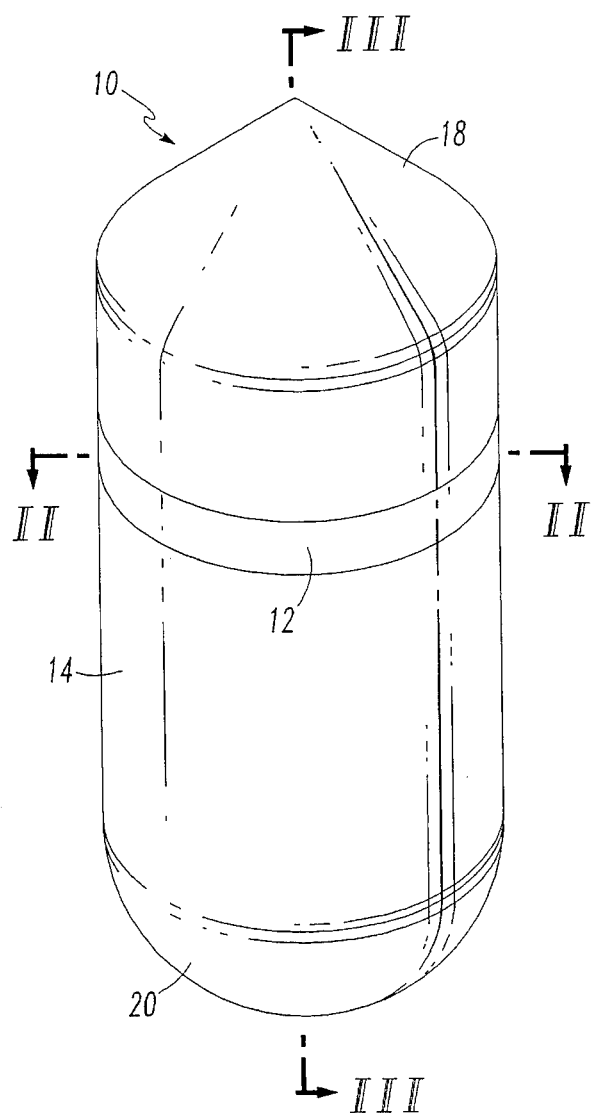
FIG. 1 is a perspective view of a first present preferred embodiment of the separator float of the present invention.
Figure 2:
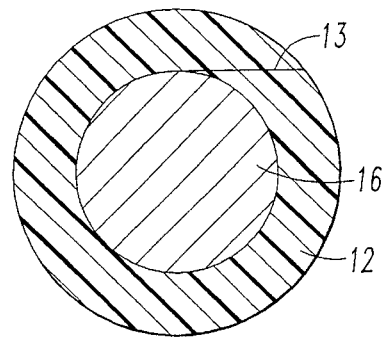
FIG. 2 is a cross-sectional view taken along line II—II of FIG. 1.
Figure 3:
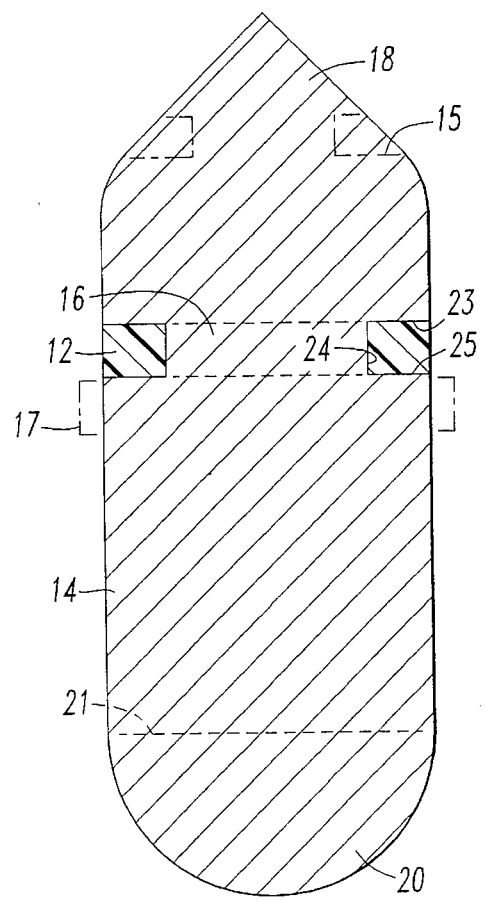
FIG. 3 is a cross-sectional view taken along line III—III of FIG. 1.

A first present preferred embodiment of the invention is shown in FIGS. 1 thru 3 in which the separator float 10 is shown to consist of a water swellable band 12 encircling the neck 16 of the float body 14. The separator has a specific gravity intermediate the light and heavy phases of blood preferably between 1.03 and 1.06. The float body 14 preferably has a conical nose cone 18 that will be directed toward the tube closure, usually a butyl rubber stopper when the float 10 is placed in a blood collection tube.

The water swellable band 12 fits into a groove 24, which surrounds neck 16. This groove may be V-shaped, concave or otherwise shaped, but we prefer the rectangular groove shown in the Figures. The band 12 is preferably a simple die cut having an outer diameter slightly less than the outer diameter of the float body 14. This washer like part is stretched over the nose cone 18 and positioned to encircle the neck 16. This water swellable washer-like band 12 will fit with slight clearance from the wall of groove 24 until it becomes exposed to the blood during centrifugation. When exposed to blood the band 12 starts to swell. The preferred material from which to form the water swellable band 12 is a the hydrophilic polyether-block-amide copolymer containing about equal weight percents nylon 6 and polyethylene glycol. One such composition is sold by Atochem under the designation "PEBAX MX 1657".

Although we prefer to place the water swellable band 12 in a groove located as shown in FIG. 1, that band could be placed in a groove 15 in the conical head 18 shown in chain line in FIG. 3. The water swellable band could also be placed around the generally cylindrical body 14 which has no groove as indicated by band 17 also shown in chain line in FIG. 3.

The separator float main body segment is generally cylindrical, but it may have a slight to moderate taper. The base end 20, of the float body 14 may be flat, slightly conical, or rounded. A hemispherical dome structure such as is shown in the drawings is appropriate for use with a molded round bottom plastic evacuated collection tube. The separator float is sized to fit within a blood collection tube. A float body having a diameter of 8.9 mm and overall length of about 28 mm works well in a 13×100 mm plastic evacuated blood collection tube. The neck 16 is then about 4.5 mm in diameter. For this body the water swellable band 12 preferably has a 4.7 mm inside diameter and 8.7 mm outside diameter, and is 1.2 mm thick. The band 12 may be cut tangentially along line 13 from the inside to the outside to facilitate seating within the groove. When in place the band has about 0.02 mm clearance between band 12 and groove walls 23 and 25. Specification of the dimensions of the float and the band affect the sealing rate of the float.

We have constructed floats from ABS polymer and silicon rubber. Other plastics which may be used are high impact polystyrene, "crystal" (clear) polystyrene, polyethylene, thermoplastic polymers and reaction molded polymers. These materials are particularly suitable for use because the readily available commercial grades of molded resins fall within the required specific gravity range critical for operation of the invention. There are higher purity FDA grades of these plastics readily available from several manufacturers.

It is also feasible to construct compound float bodies of materials other than those having specific gravities in the required ranges. For example, a float may be constructed from a polypropylene with a specific gravity of about 0.90. This material has surface properties that under certain conditions are preferable to ABS, HIPS, or clear polystyrene. The low specific gravity of polypropylene may be counterbalanced with a material of higher specific gravity. Iron wire pieces are useful as the higher density material which can be molded into the polypropylene. The quantity of this material can readily be precisely adjusted to achieve the required specific quantity value. Such a float will move with a magnet passing along the exterior of a tube containing the float. Thus, the separator float can be moved at will in the filled blood collection tube for purposes of mixing anticoagulants, in the case of plasma separation tubes. A magnet can also be used for the unique purpose of maintaining the separator float above, and out of reach of the clotting blood in the serum separator tubes.

FIG. 4 shows the separator float of FIG. 1 at the bottom of a plastic 13×100 mm evacuated plasma separator tube 30 having a conventional rubber stopper 31. The tube preferably contains lithium heparin anticoagulant, and is evacuated at the level of vacuum required to collect about 4.7 ml of blood. At the bottom of the tube there is a water-immiscible oil 32 with a specific gravity greater than that of the red blood cells. The oil's function is to isolate the water swellable band from the collected blood, and prevent activation of the water swellable band before centrifugation begins. There should be sufficient oil to maintain complete coverage of the top of the water swellable band 12 before centrifugation begins. Preferably the oil will extend a distance of 1.0 to 3.2 mm above the band 12. Polymethyl-3,3, 3-trifluoropropylsiloxane fluid, 1000 centistokes viscosity and specific gravity 1.28, has been found to work excellently, although other suitable water-immersible oils such as polyesters of adipic acid and propylene glycol may be used. After blood is collected into an evacuated blood collection tube, and the blood has been sufficiently mixed with a selected anticoagulant contained therein centrifugation begins. The oil remains in a small pool at the bottom of the collection tube, and the float separator becomes centripetally displaced to the interface formed between the blood cells and the plasma. Centrifugation at 1200 g for 10 minutes gave good separation, float emplacement, and isolation of the light and heavy phases of the blood. However, centrifugation of 1750 g was preferable, with faster, and more clearly defined blood separation and separator float emplacement.

A second preferred embodiment that can be used to obtain either serum or plasma is depicted in FIGS. 5 and 6. The separator 40 is suspended near the collection end of the evacuated blood collection tube 30 having stopper 31 by compression against three elastomeric pads 42. If desired a fewer or greater number of pads could be used. This separator float 40 is otherwise constructed like the first embodiment having a float body 44, water swellable band 45 which fits over neck 46, conical top 48 and hemispherical bottom 49. Silicone RTV single component sealant, or hot melt sealant were found to be satisfactory for the elastomeric pads 42. These pads hold the separator 40 in place during blood collection and transport. As blood is collected it may flow around the separator through channels 47 between the separator pads 42. During centrifugation the pads elongate to release the separator 40 allowing it to move to a position between the light phase and the heavy phase.

At, or slightly more distal from the water swellable seal 45, elevations may be placed at each of the locations noted for the three pads 42. These elevations can also compress against the float body 44, and support float 40. Thus, the elevations could be molded indentations of the tube 30 itself. There is also an optional hot melt attachment 43 made near the base of the conical top 48. This attachment will yield under moderate tension produced when the tube is centrifuged. The three isolating, or wall offsetting elevations, preferably are 0.5 to 0.7 mm in altitude from the wall base, depending upon the location, the taper and diameter of tube 30, and the outside diameter of float body 44.

If desired, the elastomeric pads 42 of the second embodiment could be one or more elastomer balls held against the inside tube wall by compression. The balls hold the separator float under compression, until the separator is released by rolling radially off the compressed balls into the blood during centrifugation. In this configuration, when a single ball is used, it is inserted with the separator float into the tube and squeezed tangentially against the separator band, causing the separator float to be pressed and held firmly against the opposite wall. If two or more equally spaced elastomeric balls are used, the float may be held suspended off the wall until the separator float rolls off the compressed balls. Two or three compression loci reduce wicking for uncoated floats and tube walls. The embodiment has the advantage of simplicity in manufacture, and facility of operation. There is wide selection of sizes, diameter, and elastomeric materials that can be used for the suspending roller balls.

FIG. 7 shows a third preferred embodiment having an external support for a separator float usable for serum, as well as plasma, in the widely used 16 mm×100 mm glass evacuated tube. It is one of several alternatives to the compression/friction support mechanism shown in FIGS. 5 and 6. The third embodiment is similar in shape to the first two embodiments. The separator float 50 has a float body 54 with a conical top 58 and a hemispherical bottom 59. A water swellable band 56 fits around a neck not visible in the drawing. A metal rod 55 indicated by dotted lines is molded into the body 54. Thus, when the float is placed within a test tube 30, a magnetic support ring 52 will hold the separator float in place within the center of the ring 52. The separator 50 can be made using an economical, low density, widely used disposable laboratory plastic such as polypropylene for the body of the separator float and at least one length of iron wire 2.3 mm in diameter molded within the body of the separator float. A neodymium iron boron ring magnet (30 mm O.D., 16 mm I.D., by 10 mm thick) can be used as the ring support mechanism 52. The polypropylene/iron composite separator float is sized to move freely within the blood collection tube. A present preferred float of the type depicted in FIG. 7 has a float weight of 2.406 grams, and a volume of 2.313 milliliters, with a specific gravity of 1.04 when the polypropylene has a specific gravity of 0.90, a 10.8 mm length of wire (specific gravity 7.8) is used. A water swellable band die cut from PEBAX MX 1657 polymer (specific gravity 1.19) having a 11.9 mm outside diameter and a 7.1 mm inside diameter, and being 1.6 mm thick is seated around a 7.0 mm diameter neck and within a rectangular groove 1.7 mm wide and 2.3 mm deep. The outside diameter of the polypropylene float body is 12.7 mm. The usual inside diameter of the glass tube, for which this embodiment is depicted is generally about 13.5 mm. If this were to be a 16 mm×100 mm plastic tube, design of the separator float would be partially determined by the taper of the tube.

The magnetizable compound separator float is moved into support position immediately after blood is drawn into the collection tube by vacuum. The ring magnet is moved by hand, or positioned on a rack so the plastic/magnetic separator within the blood filled tube must pass through the ring drawing and magnetically holding the magnetic separator float within the tube immediately above the clotting blood, practically adjacent to the closure 31, preventing entrapment of the separator float in the clot. When the blood has clotted, the tube may be removed from its magnet collar and centrifuged. The blood phases will be separated and the separator float will move unhindered by the clot and become emplaced. The water swellable band will operate, and the two phases become sealed and isolated form each other.

The magnetic ring 52 may be attached to or within a test tube rack shown in chain line 53. One method of use for such an arrangement is to place the separator float 55 in an evacuated test tube 30. Blood is collected into the evacuated blood collection tube 30 with magnetic core separator float 50 in the bottom of the tube. The tube is slowly inserted through the magnetic ring attached to test tube rack 53. During insertion the separator float 50 is drawn from the bottom through the collected blood 51 to the position shown in FIG. 7. There should be minimal contact between the band and the collected blood during this time resulting in minor expansion of the water swellable band 56. The tube may contain additives that need to be mixed for optimal functioning. Clot accelerators, or anticoagulants can readily and efficiently be mixed manually by several movements through the collar, if recommended, before storing the tube within the ring 52 and rack 53. The tube is maintained in the vertical position for the usual ½ hour clotting period. Then the tube is centrifuged, preferably at 1750 g for 10 minutes to obtain serum or plasma, depending on the tube additives. During centrifugation the separator will move to the interface of the light phase and the heavy phase and the washer like seal will swell.

Figure 8:
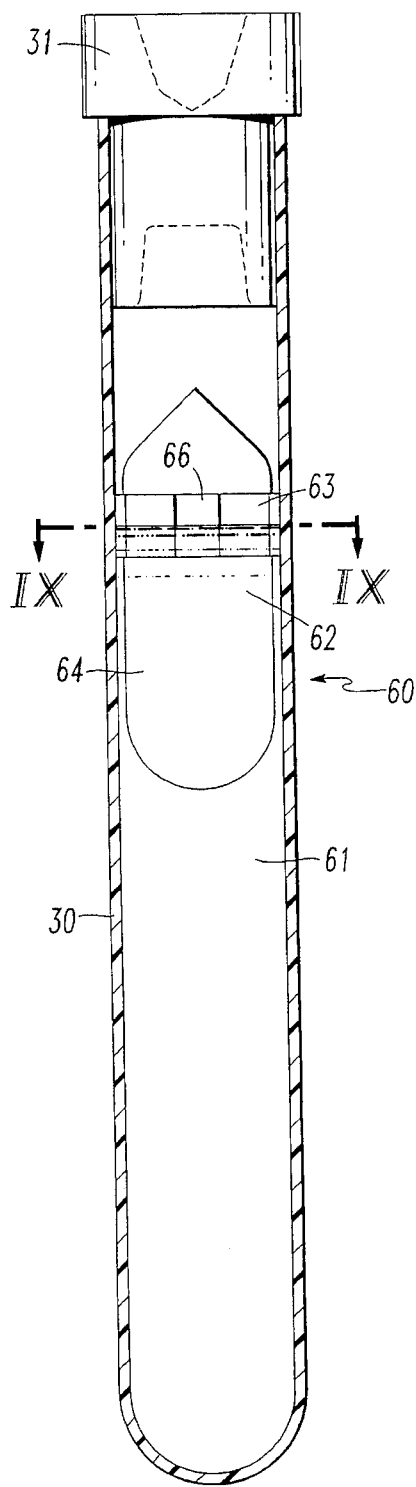
FIG. 8 is an elevational view of a fourth present preferred separator float in a blood collection tube.
Figure 9:
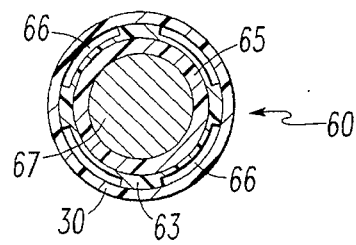
FIG. 9 is a cross-sectional view taken along line IX—IX of FIG. 8.

FIG. 8 depicts a fourth present preferred embodiment 60 in which an elastomeric tubular covering or sleeve 63 is provided around the upper section 62 of the separator float body 64 for the dual purpose of supporting the separator float 60 above the clotting blood 61, and to cover the water swellable band 65 from contact with the blood. The sleeve is shown here in a 13 mm×100 mm collection tube typically having a 10.4 mm inner diameter. This sleeve has channels 66 parallel with the axis of the blood collection tube on the exterior surface of the sleeve to permit blood flow into the evacuated tube during blood collection. Four channels between the external surface of the sleeve, and the inside wall of the blood collection tube are shown in FIG. 9. More or fewer channels may be provided. Alternatively, a segment of heat shrinkable tubing may be used to cover the water swellable band. The float may be held in place according to any of the methods described with respect to FIGS. 5 and 6. On centrifugation, the separator float 60 will be released gradually due to the friction between the elastomeric cover and the inside wall of the tube 30. This provides a controlled, delayed release of the float into the clot, permitting the clot to pack to some extent before movement of the separator float into the packed cells. The elastomeric tubular sleeve may be an extruded or molded thermoplastic material such as the silicone/polystyrene block copolymer such as sold by Concept Polymer Technologies, Inc. under the trademark "C-FLEX" or it may be silicone rubber. Dimensions of the sleeve, before it is stretched and placed over the separator float, may be 8.7 mm outside diameter, 7.1 mm inside diameter with the groove depth of 0.4 mm providing the groove diameter of 7.9 mm. This provides the tubular covering a slight amount of circumferential compressional stress on the separator float. The tubular cover 63 with the separator float contained therein should have its outside surface bonded to the inside of the collection tube 30 into which it is inserted. Although there are several ways to do this we prefer to use an adhesive. Silicon RTV sealant, or alkyl cyanoacrylate are two materials that have been found to be effective among a variety of possible choices of cements for use with thermoplastic ester evacuated blood collection tubes.

Figure 10:
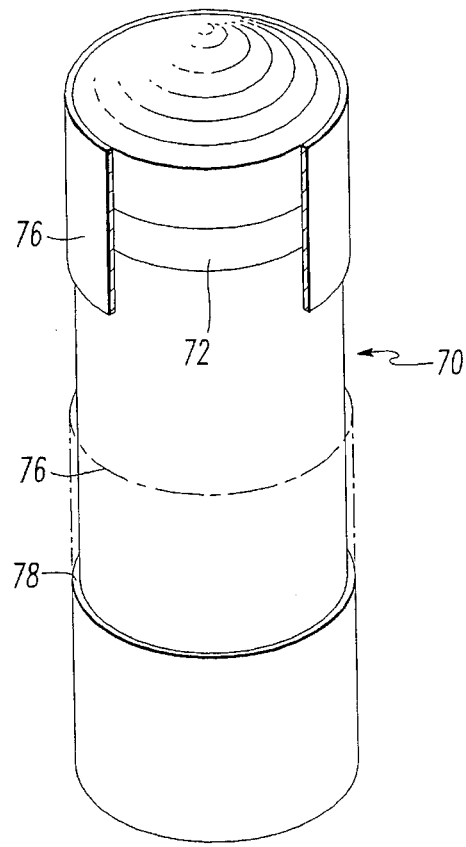
FIG. 10 is a perspective view of a fifth present embodiment of our separator float.
Figure 13:
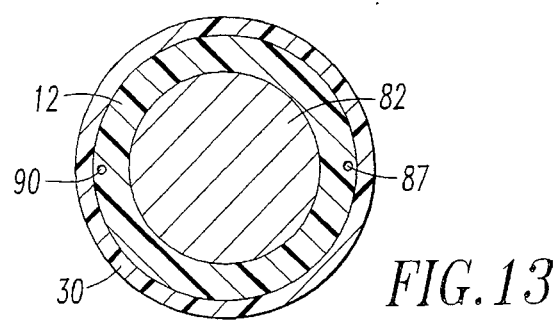
FIG. 13 is a cross-sectional view taken along the line XIII—XIII in FIG. 11.

A fifth embodiment which can be used to separate either serum or plasma, is shown in FIG. 10. It is buoyant in freshly collected whole blood and has a self-contained metal protective sleeve 76 covering the water swellable band 72 recessed in a polypropylene float 70. This float assembly is designed to have a resultant specific gravity, preferably between 1.035 and 1.045, making it buoyant in uncentrifuged blood, but merely thrusting through the surface of collected whole blood if floating unimpeded. When a tube of blood containing this free floating embodiment is centrifuged, the metal slip ring 76 moves to the position shown in chain line to expose water swellable band 72, and is prevented from slipping off the float 70 by base flange 78. Centrifugal force operates to: 1) emplace the float at its proper position relative to the phase boundaries of the separating blood; 2) cause radially directed slip/sliding of the metal ring protective sleeve covering the water swellable band; 3) separate the cellular and liquid phases of the blood; and 4) pack of the centrifuged cells with subsequent isolation of the phases by the water swellable band 72.

When the float 70 is used in an evacuated tube such as is shown in FIG. 4 to obtain plasma, blood is collected into a tube containing an anticoagulant of choice, the tube is gently rocked a few times per standard procedure, and then placed vertically and undisturbed, into a rack. The float is next lifted and held magnetically within a rack, according to the method prescribed in the description of the third embodiment shown in FIG. 7. The float is best suspended by a ring magnet of adequate strength, e.g., the neodymium iron boron type mentioned above with the wire core float of FIG. 7. The float often resists buoyant movement to the surface when unaided by external magnet force because of the relatively high viscosity of the collected blood, or some other impediment to free buoyancy within the tube of collected blood. High volume, precision stamped nickel plated metal sleeves are available at reasonable cost and have been found satisfactory for this use in the collection of whole blood for coagulation, and subsequent isolation of serum. When the float embodiments shown in FIGS. 7 and 10 are used for serum separation with generally available centrifuges in clinical laboratories, the floats are suspended in positions where they will not require the relatively high level of centripetal force needed to bypass the impacted clot, as would be if the float were to be located at the bottom of the tube, as in FIG. 4.

FIG. 10 shows polypropylene float 70, of specific gravity 0.90 and weighing 1.422 g, metal slip ring 76, with specific gravity 7.8 and weighing 0.245 g, and a water swellable band 72, of 1.19 specific gravity and weighing 0.080 g. The specific gravity of the compound float of FIG. 10 is 1.040. The float should be used with water insoluble oils of the type recommended (e.g., fluorosilicone, polyester, or similarly functioning oils of like specific gravity) so as to exclude blood from the gap between the metal ring 76 and water swellable band 72, and to reduce frictional binding between ring 76, band 72 and float 70. The gap between float 70 and slip ring 76 is 0.02 to 0.08 mm.

This invention facilitates harvesting of white cellular elements of the blood within a lighter fraction of the heavy phase of the blood. Isolation and separation, also known as harvesting of white blood cells, especially lymphocytes, from human blood is clinically necessary for histocompatibility determinations, particularly in those patients requiring organ transplants, in prognosis for treatment of AIDS, and rapidly expanding use in many other areas of DNA/genetic analysis.

To harvest lymphocytes/monocytes, blood is collected into a 13×100 mm evacuated plastic tube of the type in FIG. 4, containing sufficient EDTA, or preferred anticoagulant, and centrifuged, preferably for 10 minutes at 1750 g, and the plasma is removed from the collection tube by decanation, transfer pipetting, or other appropriate means, after a firm seal has been made against the wall of the tube. At that point the collection tube 30 will appear as shown in FIG. 11. The lymphocytes and monocytes will form a band 80 along the wall of the separator float 10 above the packed erythrocytes and granulocytes 82, and below the water swellable band 12. The lymphocytes and monocytes may be withdrawn through a syringe 86 having a needle 87 passing through the swollen band 12. Alternatively, they may be harvested by injection of an isotonic Ca++ and Mg++ free salt buffer solution 96 using a syringe 86 with a small gauge 28 needle 87 injected through the water swellable band compressed against the wall of the collection tube. A widely available disposable insulin syringe with a ½", 28 or 29 gauge needle is well adapted to inject the isotonic harvesting buffer. A transfer channel must also be used to pass the cells carried in the irrigation stream of isotonic harvesting buffer. For this purpose a small cannula 90, as for example a ¾" 26 gauge hypodermic needle inserted with forceps through the band, diametrically opposite to the buffer injection side, or a small notch at the edge of the water swellable band prior to assembly into the evacuated plasma separator tube (e.g., a semi-circle of a radius 0.4 to 0.8 mm) serves well as an irrigation exit channel. Careful injection of the buffer solution 96, which has a specific gravity less than the mass of packed red cells/granulocytes 81 below the lymphocyte/monocyte band 80, will cause the cells to be washed up and out of the space between the float and the inner wall of the collection tube, exiting through the passageway in the water swellable band into the empty space 92 previously holding the removed plasma as shown in FIG. 12. From there these cells can be drawn through pipette 88 for testing.

The sharpness of definition of the boundary between erthroctyes/granulocytes and lymphocytes/monocytes may be improved by the inclusion of a barrier material 94, which may be either a sufficiently high viscosity Newtonian liquid separator material having a specific gravity between 1.065 to 1.077, or a thixotropic gel in the same specific gravity range, either of which can be substituted for the water-immiscible oil with a specific gravity less than the red cells which was covering the float shown in FIG. 4. Such a commercially available Newtonian liquid is (79–82%)-dimethyl-(18–21%)-diphenylsiloxane copolymer, methoxy terminated, with a specific gravity 1.07, and viscosity of 650 to 700 centistokes. Examples of suitable gels for this purpose are described in Luderer et al. U.S. Pat. No. 4,190,535, which describes the formulations of gel-like oils to prepare the polymers with specific gravity ranging from 1.065 to 1.077 suitable for forming a viscous band between the packed erythrocytes/granulocytes and lymphocytes/monocytes. This band 94 separating the cellular fractions diminishes the contamination by red cells/granulocytes of lymphocytes/monocytes pushed by the injected harvesting buffer solution into the emptied plasma compartment.

The separator floats can be variously sized and shaped for particular applications. A separator float about 12 mm in diameter and about 20 mm long is usable in most of the larger diameter 16× 100 mm, or 16×125 mm evacuated blood collection tubes. A flat To obtain plasma all of the various configurations of the separator can be used in tubes containing a variety of anticoagulants, including heparin, ammonium, lithium, and sodium salt forms, or even other counterions, EDTA, or citrate. To obtain serum glass powder, silica, or other satisfactory siliceous particulate material may be used. Biologically derived clot inducers such as thrombin, prothrombin and certain snake venom derivatives may be added instead of siliceous particles to induce faster coagulation.

The separator tubes of this invention may be made from glass or molded plastic. Plastics are becoming the materials of choice because neither mechanical or thermal shock causes tubes to break and transmit blood borne infections. Also, plastic tubes can be fabricated economically with excellent dimensional precision. Plastics tubes are less fragile than glass tubes permitting centrifugation of a much higher g force with concomitantly improved separations, and reduced centrifugation time required. When plastic is used rather than glass to construct the separator tubes of this invention the separated phases may be frozen for archival storage without need for preliminary removal and transfer of the contents to separate storage vessels. The water swellable band can be modified readily to operate more rapidly, or more slowly, or to be used wherein the clearance between float and tube wall is greater, or less than depicted here. These modifications to the composition and dimensions of the band can be readily made by those skilled in the art. The choice of materials and sizing will depend upon the requirements of the user, the operations of the blood handler, the collection tubes available, and marketing and manufacturing considerations. Examples of such considerations are the volume of blood to be collected; the form of the light phase (serum or plasma); g force available by the centrifuge to be used (the higher the g force the shorter the period needed to separate the blood phases and position the separator); type of centrifugation (horizontal or angle head); vacuum or non-vacuum collection tube; use of plastic (tapered wall) or glass (parallel wall) collection tube and the presence of other materials such as anticoagulants in the tube.

Although we have shown and described certain present preferred embodiments of our separator float and methods of using the device, it should be distinctly understood that the invention is not limited thereto, but may be variously embodied within the scope of the following claims.

We claim:

1. A fluid collection tube comprising:

a. a tubular body closed at both ends and having an inner wall; and b. a separator float positioned within the tubular body, the separator float comprised i. a body comprised of a material that will not swell when exposed to water, and ii. a water swellable material covering at least a portion of the body, the water swellable material being sized and positioned so that upon being exposed to water the water swellable material will swell forming a seal within the tubular body.

2. The fluid collection tube of claim 1 also comprising a removable stopper at one closed end.

3. The fluid collection tube of claim 1 also comprising two removable stoppers, one of which is at each closed end.

4. The fluid collection tube of claim 1 also comprising an oil within the tubular body and covering at least a portion of the separator float.

5. The fluid collection tube of claim 1 also comprising a tubular sleeve attached to the inner wall of the tubular body and sized to releasably hold the separator float within the tubular body.

6. The fluid collection tube of claim 1 also comprising at least one elastomeric pad in contact with a portion of the float body and with the inner wall of the tubular body.

7. The fluid collection tube of claim 6 wherein the at least one elastomeric pad is a ball.

8. The fluid collection tube of claim 6 wherein the inner wall of the tubular body has at least one projection against which the float body rests.

9. A method of collecting blood comprising the steps of:

a. providing a blood collection tube comprised of a tubular body closed at both ends having an inner wall and a separator float positioned within the tubular body, the separator float having a specific gravity between specific gravities of a light phase and a heavy phase of the blood and comprised of:

i. a body, and ii. a water swellable material covering at least a portion of the body, the water swellable material being sized and positioned so that upon being exposed to a water containing fluid the water swellable material will swell forming a seal within the collection tube;

b. drawing blood into the collection tube; and c. centrifuging the blood collection tube thereby separating the blood into a light phase and a heavy phase during which centrifugation the separator float moves to a position between the light phase and the heavy phase and the water swellable material is exposed to water in the blood causing the water swellable material to swell and create a seal within the collection tube adjacent the separator float body.

10. The method of claim 9 also comprising the step of coating at least a portion of the tubular float before drawing blood into the blood collection tube.

11. The method of claim 10 wherein at least a portion of the float is coated with one of an oil and a grease.

12. The method of claim 9 wherein the body of the separator float contains a metal and also comprising the step of placing a magnet near the blood collection tube to hold the separator float adjacent the magnet.

13. The method of claim 12 also comprising the step of moving one of the magnet and the blood collection tube relative to one another thereby causing the separator float to move within the tubular body.

14. The method of claim 9 also comprising the steps of:

a. inserting a tube through the swelled water swellable material so that a distal end is positioned within a selected layer of blood cells below the water swellable material; and b. harvesting the blood cells within the selected layer.

15. The method of claim 14 wherein the selected layer of blood cells contains at least one of white blood cells, lymphocytes, monocytes and platelets.

16. The method of claim 14 also comprising the step of drawing the blood cells within the selected layer through the inserted tube.

17. The method of claim 14 also comprising the steps of:

a. providing a passageway through the swelled water swellable material;

b. injecting a fluid through the inserted tube into the selected layer of blood cells below the water swellable material thereby causing blood cells from the selected layer to pass through the passageway to a position above the swelled water swellable material; and c. removing those blood cells from the blood collection tube.

* * * * *